United States Patent [19]
Kruger et al.

[11] Patent Number: 5,167,816
[45] Date of Patent: Dec. 1, 1992

[54] STERILE COUPLING DEVICE FOR DRUG CONTAINER

[75] Inventors: Robert J. Kruger, Arlington Heights; Joaquin Mayoral, Mundelein, both of Ill.

[73] Assignee: Abbott Laboratories, Abbott Park, Ill.

[21] Appl. No.: 845,106

[22] Filed: Mar. 3, 1992

Related U.S. Application Data

[63] Continuation-in-part of Ser. No. 570,660, Aug. 20, 1990.

[51] Int. Cl.$^5$ .............................................. B01D 61/10
[52] U.S. Cl. ............................. 210/257.2; 210/321.83; 604/415
[58] Field of Search ................ 210/321.83, 259, 257.2, 210/335, 336; 604/414, 415, 283, 905; 141/1; 403/2, 34

[56] References Cited
U.S. PATENT DOCUMENTS
4,919,658  4/1990  Badia .............................. 604/905 X Primary Examiner—Frank Spear
Attorney, Agent, or Firm—A. Nicholas Trausch

[57] ABSTRACT

The present invention is directed to a device for sterile coupling and decoupling of a first solution system to a second solution system. The first system has a resealable member so as to allow access into the system. The device includes a housing for receiving the resealable member so as to provide a fluid tight cooperating engagement with the resealable member. A penetrable barrier is positioned in the housing across from the resealable member. A conduit in flow communication with the second system is adapted for sterile penetration of the barrier and the resealable member. An inlet and outlet duct provides a passageway between the barrier and the resealable member. The inlet is adapted for fluid flow from a source of sterilizing fluid and optionally a sterile rinsing fluid. The outlet duct receives the sterilizing fluid after is passes across and sterilizes the resealable member facing the barrier.

8 Claims, 4 Drawing Sheets

STERILE COUPLING DEVICE FOR DRUG CONTAINER

This application is a continuation-in-part of commonly assigned pending U.S. patent application Ser. No. 07/570,660, filed Aug. 20, 1990 entitled "Medical Drug Formulation and Delivery System and Reverse Osmosis Purification Device." The benefit of the filing date of this prior application is hereby claimed under 35 USC §120.

The present invention relates to a device for sterile coupling and decoupling of one medical system to a second medical system and particularly to the sterile coupling and decoupling of a sealed drug container to a delivery system by a device having a penetrable barrier disposed opposite the sealed portion of the drug container and a sterilizing fluid passageway between the barrier and the sealed portion of the container.

BACKGROUND OF THE INVENTION

It is often necessary to combine two sterile but separately contained medical solutions into a single solution before further use such as medical solutions administered to a patient. For example, many drugs are produced in concentrated solution or powdered form and are packaged in a glass vial sealed by a stopper. The drug and vial are sterilized in well-known manners such as radiation sterilization or heat sterilization by autoclaving. Likewise, a diluent solution may be packaged in a separate container such as a flexible bag and sterilized, for example, by radiation sterilization or autoclaving. Alternatively, a diluent solution such as sterile water may be produced on site by a water sterilizing device such as the low cost reverse osmosis sterile and pyrogen free water producing device of U.S. patent application Ser. No. 07/570,660, filed Aug. 20, 1990, entitled "Medical Drug Formulation and Delivery System and Reverse Osmosis Purification Device" which is hereby incorporated by reference.

It is difficult but necessary to transfer two separately contained solutions such as a drug and a diluent into a single container without introducing contamination. One example of sterilization during engagement of two components is shown by U.S. Pat. No. 4,431,424. In this arrangement a flexible casing containing a disinfectant surrounds at least one part of a first coupling element. The casing arrangement is provided with a seal to interact with an abutment on the second coupling housing during an introductory coupling movement between the components. The casing arrangement is capable of being rolled or pulled along the outside of the coupling element during the progressive engagement between the coupling components until they reach a fully engaged position allowing fluid passage.

The above described arrangement has two significant drawbacks. First, one of the coupling elements must be manufactured with the sterilizing agent attached. Second, the sterilizing agent will be intermixed with the two solutions.

The present invention is directed to a device which can be utilized with standard drug vials and flexible containers. Also the present invention is directed to a device which minimizes introducing the sterilizing agent into the mixed solution.

SUMMARY OF THE INVENTION

The present invention is directed to a device for sterile coupling and decoupling of a first compoundable system to a second solution system. The first system has a resealable member so as to allow access into the system. The device includes a housing for receiving the resealable member so as to provide a fluid tight cooperating engagement with the resealable member. A penetrable barrier is positioned in the housing across from the resealable member. A conduit in flow communication with the second system is adapted for sterile penetration of the barrier and the resealable member. An inlet and outlet duct provides a passageway between the barrier and the resealable member. The inlet is adapted for fluid flow from a source of sterilizing fluid and optionally a sterile rinsing fluid. The outlet duct receives the sterilizing fluid after it passes across and sterilizes the resealable member and the facing barrier.

A preferred embodiment of the present invention is directed to a device for sterilely coupling and decoupling of a drug container to a delivery system. The drug container typically has an open end sealed by a puncturable seal adapted for providing access into the open end. The sterile coupling device includes a housing configured and dimensioned for receiving and cooperating with the sealed open end of the container so as to provide a fluid tight cooperating engagement when the sealed open end enters the housing. A penetrable barrier is contrapositioned within the housing across from the sealed open end. The barrier is adapted for sterile penetration by a conduit of the delivery system. An inlet duct and an outlet duct are disposed through the housing and provides a passage between the barrier and the sealed open end of the drug container when positioned within the housing. The inlet duct is adapted for fluid coupling to a source of sterilizing fluid, and the outlet duct is adapted for fluid coupling to receive the sterilizing fluid after passing across the sealed open end of the drug container which faces the barrier.

Other features and advantages of the present invention will become readily apparent from the following detailed description, the accompanying drawings, and the appended claims.

DETAILED DESCRIPTION OF A PREFERRED EMBODIMENT

Figure 1:
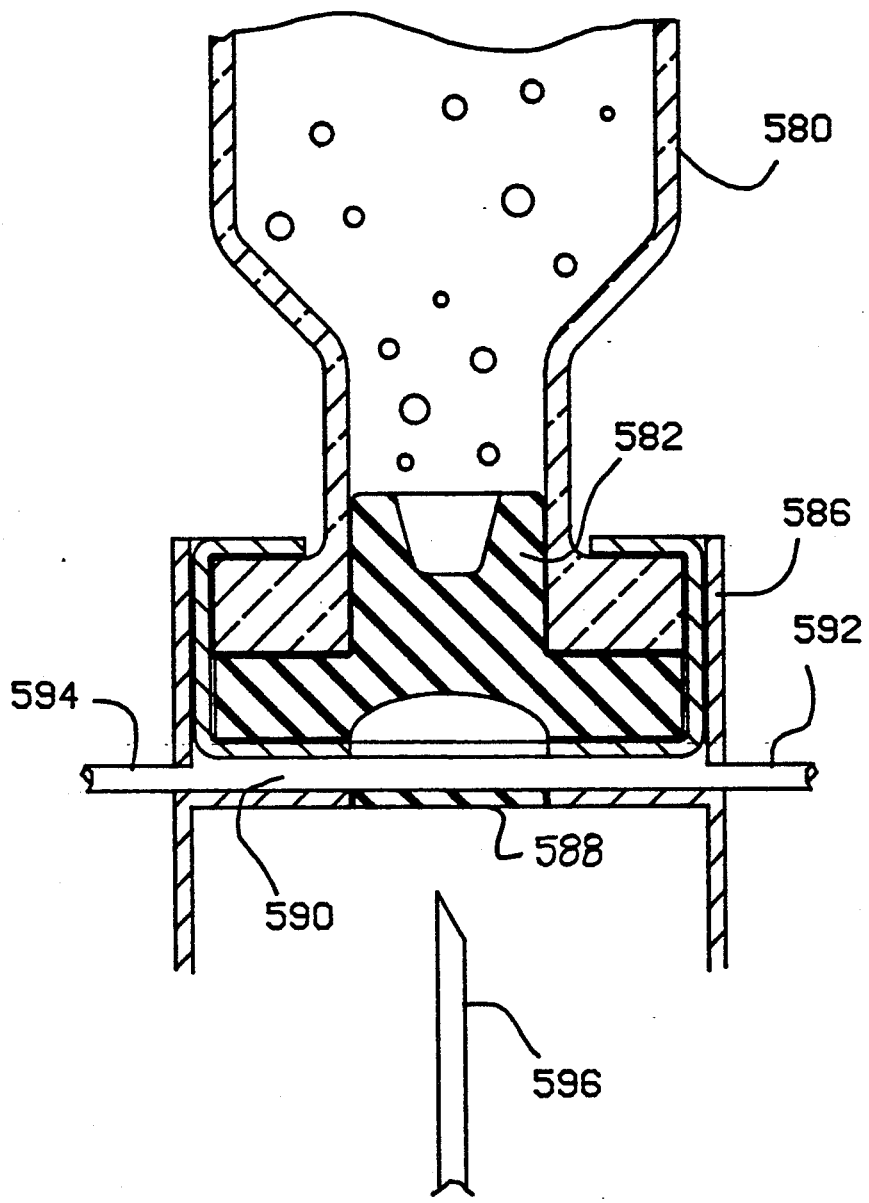
FIG. 1 depicts a device for performing a sterile connection.

While the present invention is susceptible to embodiments of various forms, there is shown in the drawings and there will hereafter be described a presently preferred embodiment, with the understanding that the present disclosure is to be considered as an exemplification of the invention, and is not intended to limit the invention to the specific embodiment illustrated.

As shown in FIG. 1, a glass bottle container 580 having a rubber septum cap 582 is placed into a receiving holder 586 having a rubber septum seal 588. The receiving holder 586 holds the rubber septum 582 in a fluidly sealed manner and is disposed adjacent to the rubber septum seal 588 so as to leave a space 590. Hydrogen peroxide solution from about 2% to about 50% concentration is then introduced into the space 590 through inlet 592 to sterilize the space 590. When the sterilization is completed the hydrogen peroxide solution may discharge through outlet 594. Subsequent to the sterilization the dual lumen needle 596 or, optionally, two needles, is moved upward puncturing the rubber septum seal 588 and the rubber septum 582 so as to sterilely connect the glass bottle container 580 to the system.

Sterile decoupling may be performed by retracting the dual lumen needle 596 below the rubber septum seal 588. The rubber septum 582 can then be decoupled from receiving holder 586 without contaminating dual lumen needle 596.

To further maintain sterile conditions, fluid flow through the system is through isolation, one-way valves so as to prevent the introduction of virus, bacteria and pyrogen from non-sterilized areas.

The above combination of procedures for maintaining sterile conditions lessens or greatly reduces the likelihood of pyrogens, bacteria and viruses entering the flow paths and thereby entering medical solutions for patient use. The system is able to maintain sterile conditions as defined by the United States Pharmacopeia.

Figure 2:
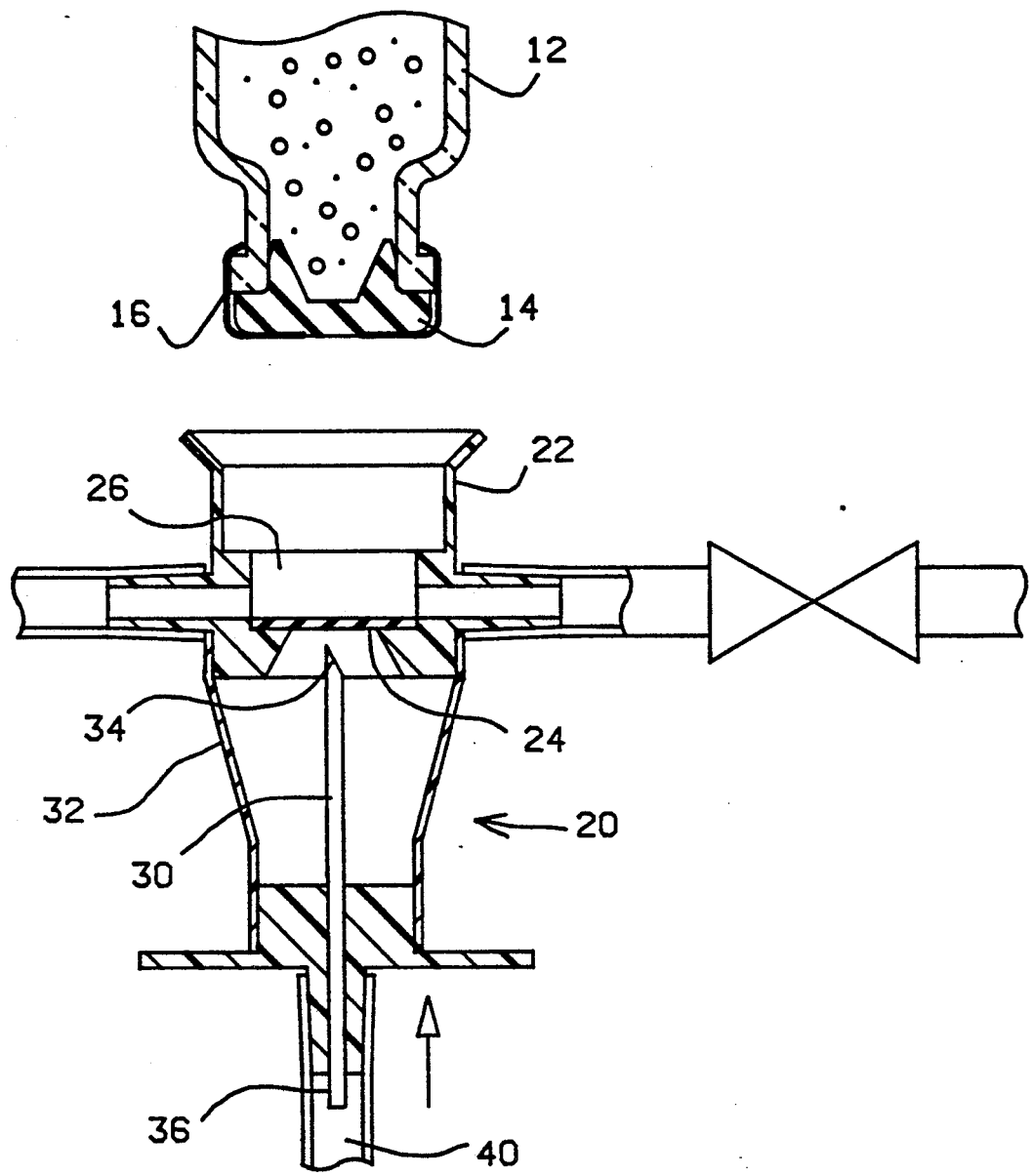
FIG. 2 shows a vertical section of the preferred embodiment of the coupling device according to the present invention before the delivery system is connected to the drug container.
Figure 3:
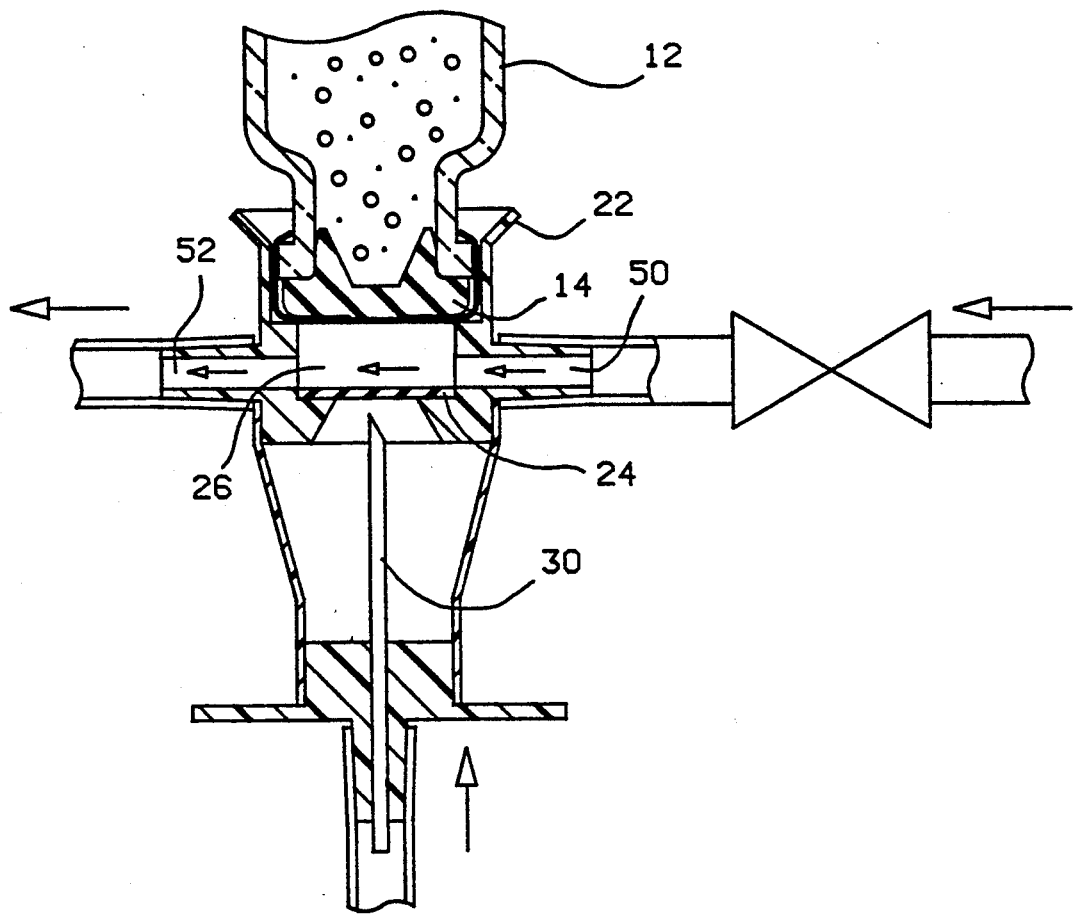
FIG. 3 shows the coupling device and drug container according to FIG. 2 during initial engagement.
Figure 4:
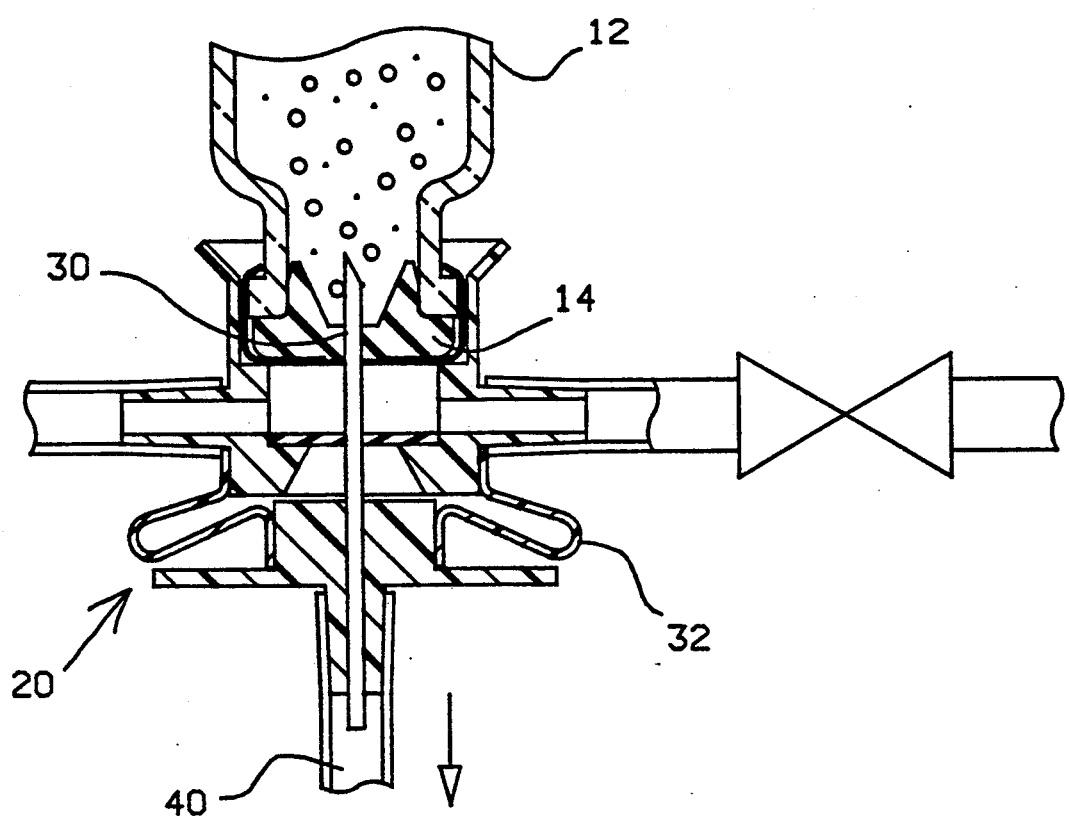
FIG. 4 shows the coupling device and drug container in the engaged position which permits solution transfer.

With reference now to FIGS. 2-4, a preferred embodiment of the invention will now be described. The first solution system is a drug container which has a penetrable and resealable seal adapted to both seal and reseal the open end and to allow access into the open end of the container. For example, as shown in FIG. 2, the drug container may be a standard glass vial 12 in common use to contain medical solutions or powders such as a concentrated drug. The open end of the vial is sealed by a medical grade rubber stopper 14. An annular metal overcap 16 is placed over the stopper to hold the stopper onto the glass vial. Alternatively, the drug container could be a flexible plastic bag or semi-rigid container having a plastic port member with a resealable septum on the end, all of which are typical products in common medical use today.

A coupling and delivery device 20 includes a receiving holder 22. The receiving holder is configured and dimensioned to receive and provide a fluid tight engagement to the particular sealed open end of the drug container used with the system.

The coupling device 20 also includes barrier seal 24 positioned opposite and generally parallel to the engaged seating position of the sealed open end 14 of the container. A passageway 26 remains between the sealed open end 14 and the barrier seal 24. The barrier seal 24 preferably is a resealable seal such as a latex membrane capable of being punctured and resealing.

A lower containment assembly 32 is sealed to the barrier seal 24 and includes a conduit 30. The conduit is adapted for sterile penetration of the barrier seal 24 and container reseal 14 as, for example, by sharp end 34. The conduit 30 is preferably a dual lumen needle or plastic spike as previously described and is connected at its distal end 36 to a second solution system 40 such as a drug delivery system. The drug delivery system may be, for example, a supply of diluent fluid such as sterile water or dextrose as for example a flexible I.V. bag or a continuously processing system such as the previously mentioned RO water purifying device.

The conduit 30 is preferably dual lumen so as to provide a solution transfer passage from and a container venting passage to rigid container such as vial 12. The conduit 30 can optionally be single lumen if the container 12 is vented or if the container 12 is flexible and doesn't require venting for solution to flow through the conduit.

Referring now to FIG. 3, the receiving member 22 holds the resealable stopper 14 of the drug container in a fluidly sealed manner across from the barrier seal 24 so as to leave a passageway 26 between the stopper and the barrier.

An inlet duct 50 and an outlet duct 52 are disposed in the housing between the barrier seal 24 and the resealable stopper 14, in flow communication with the passageway 26. The inlet duct is adapted for fluid coupling to a source of sterilizing fluid such as hydrogen peroxide vapor from about 2% to about 50% concentration as taught, for example, in commonly assigned U.S. patent application Ser. No. 07/510,317, filed Apr. 17, 1990 entitled "Method for Sterilizing an Enclosure with Noncondensing Hydrogen Peroxide-Containing Gas", which is incorporated herein by reference. Alternatively, other sterilizing fluids such as preferably liquid hydrogen peroxide or sodium hypochlorite or povidone iodine may be passed through the inlet duct 50. When the sterilization of passageway 26 is complete, the sterilizing solution may be discharged through the outlet duct 52.

Optionally a rinsing solution such as sterile water may also be connected to inlet duct 50. The rinse solution can be passed through the passage 26 to dilute or flush any of the residual sterilizing fluid that remains so as to minimize intermixing with the solutions in either of the systems or contact with the system operator.

Subsequent to the sterilization, as seen in FIG. 4, the conduit 30 may be moved forward to puncture the barrier seal 24 so as to sterilely connect the system 40 to the container 12. The conduit is preferably a dual lumen needle or, optionally, two needles since in most instances the drug container 12 is sealed and unvented. In certain instances, the conduit may be a single lumen needle when the drug container contains a pressurized fluid or when the drug container is vented or flexible.

The containment assembly 32 is a flexible material which allows the walls to be folded so that the conduit 30 can penetrate the container stopper 14. A hydraulic, solenoid driven or manual mechanism will produce the desired motion and can be controlled accordingly.

Sterile decoupling may be performed by retracting the conduit below the barrier seal 24. The container 12 can then be decoupled from the receiving holder 22 without contaminating the conduit 30 or the system 40. Subsequent sterile connections can then be made to the system 40.

The above described coupling and decoupling device of the present invention is extremely useful with a low cost, fluid purifying device such as the reverse osmosis sterile and pyrogen free water producing device of U.S. patent application Ser. No. 07/570,660, filed Aug. 20, 1990, entitled "Medical Drug Formulation and Delivery System and Reverse Osmosis Purification Device" previously incorporated by reference. The RO device can provide a sterile diluent for diluting the solution in container 12 prior to delivery to a patient. Also, the RO device can provide a sterile rinse fluid to flush the passageway 26.

To further maintain sterile conditions and control fluid flow, one-way valves may be provided in both the inlet 50 and outlet 52 ducts and in the connection 40 to the delivery system to prevent the introduction of virus, bacteria and pyrogen.

From the foregoing, it will be observed that numerous modifications and variations can be affected without departing from the spirit and scope of the novel concept of the present invention. It is to be understood that no limitation respect to the specific embodiment is intended or should be inferred. This disclosure is intended to cover by the appended claims, all such modifications as fall within the scope of the claims.

We claim:

1. A device for sterile coupling and decoupling of a first system to a second system, the first system having a resealable member so as to allow access into the system, the device comprising:
    a housing configured and dimensioned for receiving and cooperating with the resealable member so as to provide a fluid tight cooperating engagement when the resealable member enters said housing;
    barrier means disposed within said housing and positioned across from said resealable member;
    a conduit connected to the second system and adapted for sterile penetration of said barrier and said resealable member; and
    an inlet duct and an outlet duct disposed through said housing and disposed between said barrier means and the resealable member when positioned within said housing, said inlet duct adapted for fluid flow from a source of sterilizing fluid, and said outlet duct adapted for fluid flow to receive said sterilizing fluid after passing across the resealable member facing said barrier means.

2. The device of claim 1 wherein said inlet duct, said outlet duct, said barrier means and said resealable member when positioned in said housing form a fluid flow passageway.

3. The device of claim 2 further comprising a source of sterile rinsing fluid adapted for flow connection to the inlet duct so as to flush residual sterilizing fluid from the fluid flow passageway.

4. The device of claim 1 wherein said conduit is a dual lumen conduit.

5. The device of claim 4 wherein said dual lumen conduit comprises a solution transfer lumen and a system venting lumen.

6. A device for sterile coupling and decoupling of a drug container to a delivery system, the container having an open end and a puncturable seal adapted to seal the open end and to allow access into the open end, the device comprising;
    a housing configured and dimensioned for receiving and cooperating with the container so as to provide a fluid tight cooperating engagement when the sealed open end enters said housing;
    barrier means disposed within said housing and positioned across from said sealed open end;
    a conduit connected to the delivery system and adapted for sterile penetration of said barrier; and
    an inlet duct and an outlet duct disposed through said housing and disposed between said barrier means and the sealed open end of the container when positioned within said housing, said inlet duct adapted for fluid flow from a source of sterilizing fluid, and said outlet duct adapted for fluid flow to receive said sterilizing fluid after passing across the sealed open end facing said barrier means.

7. The device of claim 6 wherein said conduit is a dual lumen piercing device having a fluid transfer lumen and a system venting lumen.

8. The device of claim 6 wherein the drug container is a flexible container and the conduit is a single lumen piercing device.

* * * * *